United States Patent
Schöller et al.

(10) Patent No.: US 8,167,812 B2
(45) Date of Patent: May 1, 2012

(54) DEVICE AND METHOD FOR DETECTING OBSTRUCTIVE EVENTS

(75) Inventors: Bernhard Schöller, Karlsruhe (DE);
Sergey Velykokhatko, Karlsruhe (DE);
Matthias Schwaibold, Karlsruhe (DE)

(73) Assignee: Weinmann Gerate fur Medizin GmbH & Co. KG, Hamburg (DE)

( * ) Notice: Subject to any disclaimer, the term of this patent is extended or adjusted under 35 U.S.C. 154(b) by 1293 days.

(21) Appl. No.: 11/893,975

(22) Filed: Aug. 16, 2007

(65) Prior Publication Data

US 2008/0058665 A1 Mar. 6, 2008

(30) Foreign Application Priority Data

Aug. 24, 2006 (DE) .......... 10 2006 041 015

(51) Int. Cl.
*A61B 5/08* (2006.01)
*A61M 16/00* (2006.01)
(52) U.S. Cl. ............... 600/529; 128/204.18
(58) Field of Classification Search .......... 600/529; 128/204.23
See application file for complete search history.

(56) References Cited

U.S. PATENT DOCUMENTS

| | | | | |
|---|---|---|---|---|
| 5,617,846 A * | 4/1997 | Graetz et al. | | 128/204.21 |
| 5,704,345 A * | 1/1998 | Berthon-Jones | | 128/204.23 |
| 6,142,952 A * | 11/2000 | Behbehani et al. | | 600/533 |
| 6,622,726 B1 * | 9/2003 | Du | | 128/204.26 |
| 2003/0111079 A1 * | 6/2003 | Matthews et al. | | 128/204.18 |
| 2005/0211248 A1 * | 9/2005 | Lauk et al. | | 128/204.23 |
| 2009/0107498 A1 * | 4/2009 | Plattner et al. | | 128/204.23 |
| 2011/0036352 A1 * | 2/2011 | Estes et al. | | 128/204.23 |

FOREIGN PATENT DOCUMENTS

| | | | |
|---|---|---|---|
| EP | 0 705 615 | | 4/1996 |
| WO | WO-93/09834 | * | 5/1993 |
| WO | WO-2006/084456 | * | 8/2006 |

OTHER PUBLICATIONS

"Obstructive Pressure Peak as Control Parameter of Automatic CPAP Devices" Nilius et al. Department of Pneumology, Klinik Ambrock, University of Witten-Herdecke, D-58091 Hagen/Germany. Copyright 2006.*

* cited by examiner

*Primary Examiner* — Patricia Mallari
*Assistant Examiner* — Meredith Weare
(74) *Attorney, Agent, or Firm* — Lucas & Mercanti, LLP; Klaus P. Stoffel

(57) ABSTRACT

In a method for detecting a physiological signal at least one ventilation parameter is measured. The device for detecting a physiological signal has at least one sensor for measuring a ventilation parameter and a control unit for the ventilation pressure. A device for monitoring at least one ventilation parameter while respiratory gas is being supplied to a patient is provided with a sensing device for detecting the behavior of the ventilation parameter as a function of time.

19 Claims, 3 Drawing Sheets

DEVICE AND METHOD FOR DETECTING OBSTRUCTIVE EVENTS

BACKGROUND OF THE INVENTION

1. Field of the Invention

The present invention relates to a method for detecting a physiological signal, in which at least one ventilation parameter is measured and analyzed to control a ventilation pressure.

The invention also concerns a device for detecting a physiological signal, which has a sensor for measuring a ventilation parameter and a control unit for producing a ventilation pressure.

The invention further concerns a device for monitoring at least one ventilation parameter while respiratory gas is being supplied to a patient, which has a sensing device for detecting the behavior of the ventilation parameter as a function of time.

2. Description of the Related Art

Large numbers of persons suffer from sleep disorders, which affect the well-being of these persons during the day and in some cases have an adverse effect on their quality of life. One of these sleep disorders is sleep apnea, which is treated primarily by CPAP therapy (CPAP=continuous positive airway pressure), in which a flow of respiratory gas is continuously supplied to the patient through a nasal mask as the patient sleeps. A hose connects the mask with a ventilator, which includes a blower that produces a gas flow with, for example, a positive pressure of 5 to 20 mbars.

The gas flow is supplied to the patient either at constant pressure or, to relieve the respiratory work of the patient, at a lower level during expiration.

The lowering and raising of the ventilation pressure are effected on the basis of various events identified by the device and by measured respiratory parameters.

The following are examples of such events: mouth expiration, mouth breathing, leakage, swallowing, speaking, sneezing, coughing, increase in respiratory flow, decrease in respiratory flow, flattening of the respiratory flow, cessation of respiratory flow, increase in resistance, leakage, apnea, hypopnea, snoring, inspiration, expiration, interruption of breathing, increase in respiratory volume, decrease in respiratory volume, inspiratory constriction of the respiratory flow, inspiratory peak flow, decrease in the inspiratory flow after peak flow, second maximum of the inspiratory peak flow, increase in the pressure of the respiratory gas, decrease in the pressure of the respiratory gas, increase in the flow of the respiratory gas, decrease in the flow of the respiratory gas, increase in the volume of respiratory gas delivered, decrease in the volume of respiratory gas delivered.

SUMMARY OF THE INVENTION

The object of the present invention is to improve a method of the aforementioned type in such a way that pressure control is optimized.

Another object of the present invention is to construct a device of the aforementioned type for optimization of pressure control.

A further object of the present invention is to further optimize a device of the aforementioned type.

The three objects listed above are met by the three combinations of features specified at the beginning.

The method of the invention is aimed at detecting obstructive apneas, explicitly, at the end of an apnea, since these are usually difficult to distinguish from central apneas or difficult to detect at all. If apneas are detected exclusively by an approximately zero line in the flow, the distinction obstructive/central is not possible. Oscilloresistometry is available for this purpose (EP 0 705 615 B1), but it requires considerable design expense, results in higher production costs, and is not suitable for all types of masks.

The method of the invention makes it possible to detect obstructive apnea more simply and reliably than methods that make use of pressure to detect the obstructive apnea. The device used in this method has a pressure sensor that senses the pressure signals in the patient system, which consists, for example, of a respiratory hose, pressure hose, patient interface, expiratory element, etc., and feeds them to an analyzer. The analyzer analyzes the pressure curve and makes use of the fact that, at the end of an episode of obstructive apnea, an abrupt pressure drop, obstructive pressure peak (OPP) can usually be measured when the respiratory passages suddenly open, and the pressure between the mask and the respiratory tract must be equalized.

During the obstructive apnea, the lower respiratory tract of the patient is disconnected from the system respiratory hose/mask/upper respiratory tract, so that typically a pressure difference between the mask and the lower respiratory tract develops as a result of the respiratory excursions of the patient. When the respiratory tract reopens, this results in a pressure equalization, which can be detected as a pressure surge in the mask or in the patient system, as an abrupt increase in the rotational speed of the blower, or as an abrupt flow pulse. Typically, it is rapidly equalized by the control response of the therapeutic apparatus, but overshooting can occur, and this can lead to abrupt pressure increases.

In central apneas, the lower respiratory tract always remains connected with the system respiratory hose/mask/upper respiratory tract, and there are no respiratory excursions of the patient. Therefore, a pressure difference that must be equalized at the end of the apnea cannot arise.

These effects appear especially when the patient is already connected to the therapeutic apparatus and is receiving therapy, i.e., when a certain pressure is already being applied in the respiratory mask.

Changes in the respiratory tract are usually accompanied by fluctuations near the maxima of the flow curve. These changes can be caused by obstruction or can have other causes, so that obstruction cannot be definitely identified.

However, if the values of the pressure curve are also considered, the previously mentioned pressure peaks in the time interval of the maxima can also be recorded and recognized during obstructive respiratory tract changes, since the vibration of the tissue surrounding the upper respiratory passages represents a further cause of obstructive pressure peaks—especially at the instant of opening or closing. In this regard, it is important inspiratory and expiratory pressure peaks can arise due to artifacts, such as coughing, speaking, swallowing, leakage, and mouth expiration, and are an indication that the inspiratory pressure peaks in the corresponding segment are possibly not a reliable indication of obstructions. These pressure peaks make it possible to draw conclusions about the type of instruction.

The various features of novelty which characterize the invention are pointed out with particularity in the claims annexed to and forming a part of the disclosure. For a better understanding of the invention, its operating advantages, specific objects attained by its use, reference should be made to the drawing and descriptive matter in which there are illustrated and described preferred embodiments of the invention.

DESCRIPTION OF THE PREFERRED EMBODIMENTS

Figure 1:
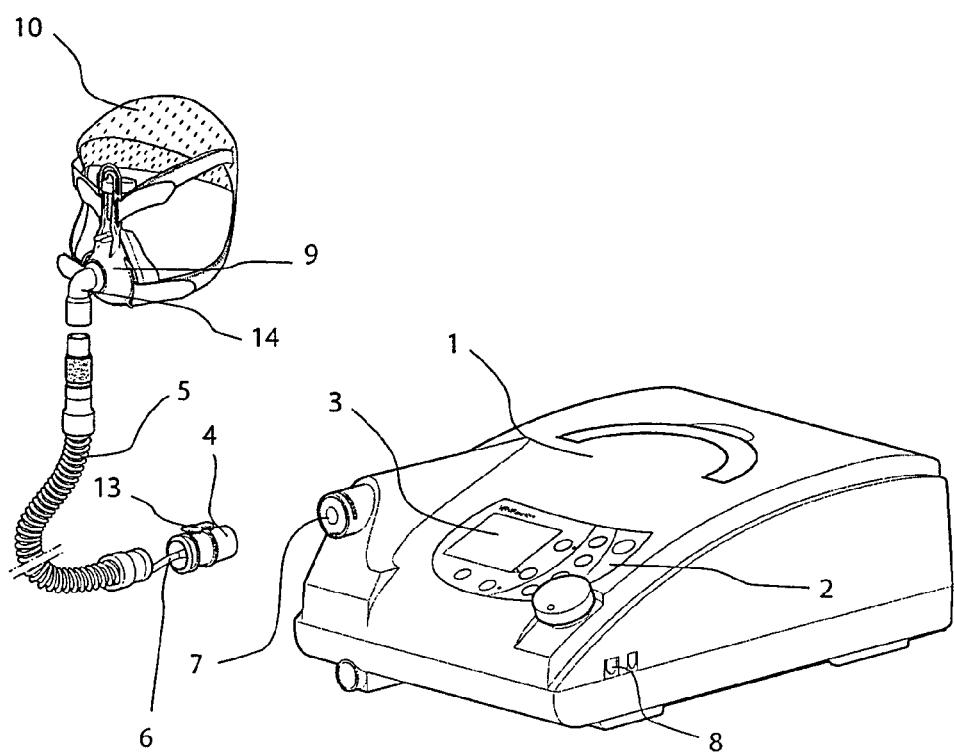
FIG. 1 shows a basic design of a ventilator.

FIG. 1 shows the basic design of a ventilator. A respiratory gas pump is installed inside an apparatus housing 1, which has an operating panel 2 and a display 3. A connecting hose 5 is attached by a coupling 4. The coupling 4 can be quickly and easily connected to the ventilator by an operating element 13. An additional pressure-measuring hose 6, which can be connected with the ventilator housing 1 by a pressure input connection 7, can run along the connecting hose 5. To allow data transmission, the ventilator housing 1 has an interface 8. An expiratory element 14 is installed in an expanded area of the connecting hose 5 that faces away from the apparatus housing 1. Not shown are a pressure gauge and a flowmeter, which are located near the patient in the vicinity of the patient interface, or in the vicinity of the ventilator, or in the vicinity of the connecting hose.

A mask 9, which is held on the patient's head by a headband 10, can also be attached by the respiratory hose 5.

Figure 2:
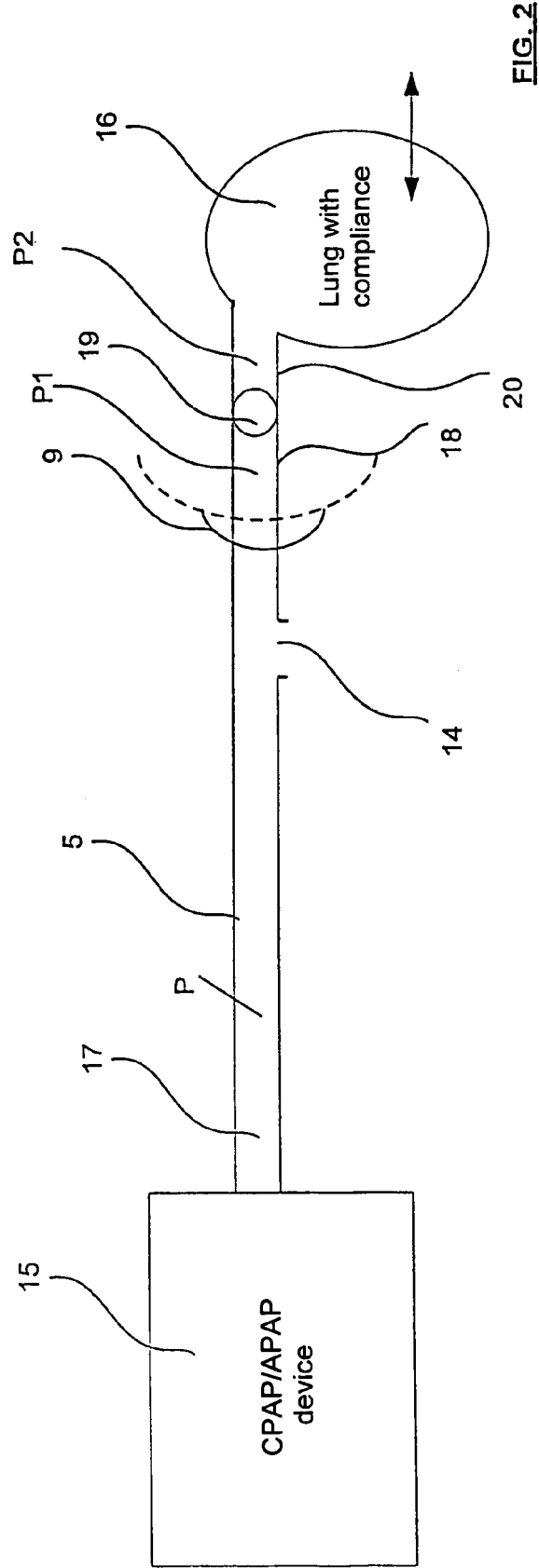
FIG. 2 is a schematic representation of a ventilator with the detection of flow fluctuations.

According to the embodiment in FIG. 2, a ventilator 15 for carrying out CPAP or APAP ventilation is connected with a mask 9 by a connecting hose 5. The connecting hose 5 has a constant opening as the expiratory element 14. The patient's lung 16 is also shown. A supply pressure P produced by the ventilator is present in the area of a section of line 17. In the vicinity of the mask 9, a pressure P1 that corresponds to a CPAP pressure can be determined at a measuring point 18 on the patient side. A possible obstruction can occur in an airway 19, and a pressure P2 is present on the other side of the obstruction from the measuring point 18 at a measuring point 20 in the airway 19.

Excursions produced during an episode of apnea lead to pressure fluctuations at the measuring point 20.

Figure 3:
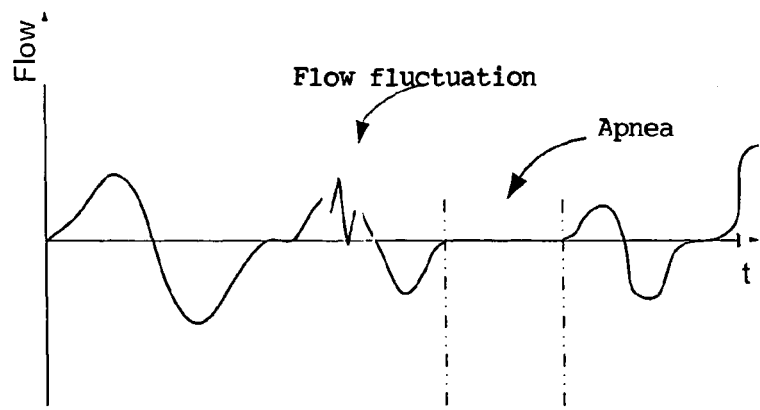
FIG. 3 shows a flow curve in obstructive apnea and in central apnea.

FIG. 3 shows a flow curve that is typical in both obstructive and central apnea. Almost no flow is occurring during the apnea due to the obstruction of the airway, while typical flow fluctuation is observed before the occurrence of the apnea. A typical flow fluctuation is referred to as flattening and describes a flattening of the flow curve in the vicinity of the maximum flow. In accordance with the invention, the beginning of the apnea is identified at least by a flow fluctuation, and the end of the apnea is identified at least by a pressure fluctuation.

Figure 4:
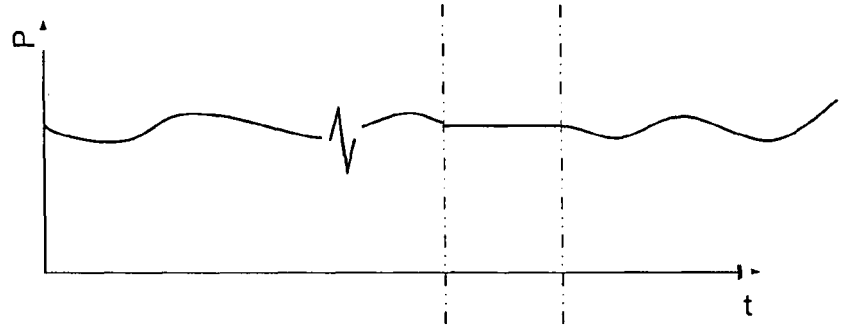
FIG. 4 shows a pressure curve in central apnea.

FIG. 4 shows a pressure curve that corresponds to the flow curve in FIG. 3 during the occurrence of an episode of central apnea. Typical small pressure fluctuations in the mask pressure occur during breathing due to the use of a pressure controller. At the time of the flow fluctuation, a corresponding pressure fluctuation also occurs in the case of central apnea.

Figure 5:
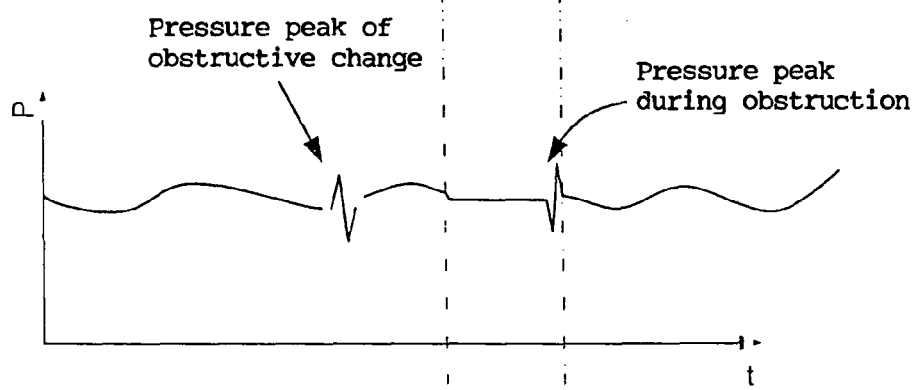
FIG. 5 shows a pressure curve in obstructive apnea.

FIG. 5 shows a pressure curve associated with the occurrence of an episode of obstructive apnea. As in the case of the pressure curve in FIG. 4, we again find a pressure fluctuation corresponding to the flow fluctuation, but in this case there is also a brief additional pressure change shortly before the end of the apnea when the airways open due to a pressure equalization between the mask and the respiratory tract. The time axes of FIGS. 3, 4, and 5 are identical.

If an episode of apnea is detected in the flow signal, the detection unit looks for short, significant deflections in the pressure channel. "Short" means much shorter than a typical respiratory period of a patient. Possible artifacts caused by movements of the patient, hose, etc., or by the patient's heartbeat are tuned out. This is accomplished by evaluating only deflections which occur in the last interval of the apnea or during the first breath after the apnea and which are greater than a detection threshold value. In an especially preferred embodiment of the invention, this threshold value can be automatically adaptively adjusted to allow optimum separation of artifacts and pressure deflections caused by obstructions.

For example, in accordance with the invention, a pressure mean value is determined during an episode of apnea. If the pressure mean value changes or the amplitude of the pressure mean value rises, this indicates the end of an episode of apnea. A change in the pressure mean value is preferably used as a control parameter for controlling the ventilator.

To achieve optimum therapy, this detection threshold value is additionally varied as a function of the therapeutic pressure, specifically, in such a way that, at low therapeutic pressures, the sensitivity of the detection of episodes of obstructive apnea is increased, and at higher therapeutic pressures, the specificity of the detection of episodes of obstructive apnea is increased.

Especially in the case of partial obstructions, the pressure signal and the flow signal are considered together, and the ventilator is automatically controlled on the basis of the pressure and/or flow signals. Definable irregularities in the behavior of the pressure signal and the flow signal are detected and used as control parameters for controlling the ventilator.

While specific embodiments of the invention have been described in detail to illustrate the inventive principles, it will be understood that the invention may be embodied otherwise without departing from such principles.

We claim:

1. A method for analyzing a physiological signal, comprising:
    measuring at least one first ventilation parameter with a pressure sensor that senses pressure signals in a patient system;
    feeding the pressure signals to an analyzer;
    analyzing a pressure curve in the analyzer, wherein the analyzer is configured to measure an abrupt pressure drop, obstructive pressure peak (OPP), when respiratory passages suddenly open at the end of an episode of obstructive apnea and pressure between a mask and a respiratory tract must be equalized; and
    identifying, via the analyzer, an obstructive apnea by the measured obstructive pressure peak at the end of an episode of obstructive apnea.

2. The method in accordance with claim 1, wherein analyzing the pressure curve comprises comparing the behavior of the at least one first ventilation parameter with stored data.

3. The method in accordance with claim 2, wherein analyzing the pressure curve further comprises determining the end of an episode of obstructive apnea on the basis of the comparison.

4. The method in accordance with claim 1, further comprising analyzing the pressure drop for controlling a ventilator.

5. The method in accordance with claim 1, further comprising using the identified apnea to control a ventilator.

6. The method in accordance with claim 1, further comprising determining at least a flow curve as a second ventilation parameter.

7. The method in accordance with claim 1, wherein the at least one first ventilation parameter comprises at least a pressure curve.

8. The method in accordance with claim 6, wherein analyzing the pressure curve comprises carrying out a pressure measurement near a maximum of the flow curve.

9. The method in accordance with claim 1, further comprising detecting, via a detection unit, short and significant deflections in the pressure curve after an episode of apnea has been detected.

10. The method in accordance with claim 9, further comprising evaluating only the deflections which occur in a last interval of the apnea or during a first breath after the apnea and which are greater than a detection threshold value.

11. The method in accordance with claim 10, further comprising adaptively adjusting the threshold value automatically.

12. The method in accordance with claim 10, further comprising varying the threshold value as a function of the therapeutic pressure.

13. The method in accordance with claim 12, wherein varying the threshold value comprises increasing the sensitivity of the detection of episodes of obstructive apnea at low therapeutic pressure, and increasing the specificity of the detection of episodes of obstructive apnea at higher therapeutic pressures.

14. The method in accordance with claim 1, wherein analyzing the pressure curve comprises detecting inspiratory and expiratory pressure fluctuations.

15. The method in accordance with claim 1, wherein analyzing the pressure curve comprises determining a pressure mean value during an episode of apnea, and evaluating a change in the pressure mean value as a parameter for controlling the ventilator.

16. A device for analyzing a physiological signal, comprising:
    at least one pressure sensor for measuring a ventilation parameter;
    a control unit for producing a ventilation pressure; and
    an analyzer for analyzing a pressure curve,
    wherein the pressure sensor is configured to sense pressure signals in a patient system and feed the pressure signals to the analyzer,
    wherein the analyzer is configured to measure an abrupt pressure drop, obstructive pressure peak (OPP), when respiratory passages suddenly open at the end of an episode of obstructive apnea and pressure between a mask and a respiratory tract must be equalized, and identity an obstructive apnea by the measured obstructive pressure peak at the end of an episode of obstructive apnea.

17. A device for monitoring at least one ventilation parameter while respiratory gas is being supplied to a patient, the monitoring device comprising:
    a sensing device for detecting the behavior of the ventilation parameter as a function of time; and
    an analyzer configured to measure an abrupt pressure drop, obstructive pressure peak (OPP), when respiratory passages suddenly open at the end of an episode of obstructive apnea and pressure between a mask and a respiratory tract must be equalized, and identity an obstructive apnea by the measured obstructive pressure peak at the end of an episode of obstructive apnea,
    wherein the sensing device comprises a pressure sensor for sensing pressure signals, which is configured to determine the curve of a pressure signal in a patient system, and feed the pressure signal to the analyzer.

18. The device in accordance with claim 17, further comprising an evaluation unit, in communication with the analyzer, for determining well-defined fluctuations of the pressure signal.

19. The device in accordance with claim 18, wherein the analyzer makes the analytical result of the well-defined pressure fluctuations determined by the evaluation unit available to an automatic controller as a control parameter for controlling a respiratory gas source of a ventilator.

* * * * *